United States Patent
Spencer et al.

(10) Patent No.: US 6,501,547 B1
(45) Date of Patent: *Dec. 31, 2002

(54) HAND-HELD PRODUCE RECOGNITION SYSTEM AND PRODUCE DATA COLLECTOR

(75) Inventors: Michael A. Spencer, Suwanee, GA (US); Donald A. Collins, Jr., Lawrenceville, GA (US)

(73) Assignee: NCR Corporation, Dayton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/507,369

(22) Filed: Feb. 18, 2000

(51) Int. Cl.[7] .............................. G01J 3/18; G01J 3/42; G06K 7/10
(52) U.S. Cl. .................. 356/328; 356/328; 235/462.06; 235/462.11
(58) Field of Search ................................ 356/328, 326, 356/430, 428, 446, 240, 416, 402–411, 300, 319; 235/462.06, 462.11

(56) References Cited

U.S. PATENT DOCUMENTS

| | | | |
|---|---|---|---|
| 4,060,327 A | * 11/1977 | Jacobowitz et al. | .......... 356/96 |
| 5,166,755 A | 11/1992 | Gat | ............................ 356/419 |
| 5,267,178 A | 11/1993 | Berner | |
| 5,319,437 A | * 6/1994 | Van Aken et al. | .......... 356/326 |
| 5,483,339 A | 1/1996 | Van Aken et al. | .......... 356/326 |
| 5,540,113 A | 7/1996 | Takei | ........................ 74/424.8 |
| 5,546,475 A | 8/1996 | Bolle et al. | .................. 382/190 |
| 5,630,402 A | 5/1997 | Devine et al. | ............... 123/508 |
| 5,867,265 A | * 2/1999 | Thomas | ....................... 356/328 |
| 5,869,840 A | 2/1999 | Helton | |
| 6,332,573 B1 | * 12/2001 | Gu et al. | ................ 235/462.06 |

FOREIGN PATENT DOCUMENTS

| | | |
|---|---|---|
| EP | 0921381 | 6/1999 |
| WO | 9708537 | 3/1997 |
| WO | 9746856 | 12/1997 |

* cited by examiner

Primary Examiner—Frank G. Font
Assistant Examiner—Layla Lauchman
(74) Attorney, Agent, or Firm—Paul W. Martin; Priest & Goldstein, PLLC

(57) ABSTRACT

A hand-held produce data collector which captures wavelength information from a produce item. The produce data collector includes a light emitter for illuminating a produce item, collecting optics for collecting light reflected from the produce item and separating the reflected light into a plurality of wavelength portions of light, a photosensor for capturing wavelength information from the wavelength portions of light, control circuitry, and a hand-held housing containing the light emitter, the collecting optics, the photosensor, and the control circuitry. The control circuitry may store reference wavelength information and compare the captured wavelength information to the reference wavelength information to identify the produce item.

28 Claims, 3 Drawing Sheets

HAND-HELD PRODUCE RECOGNITION SYSTEM AND PRODUCE DATA COLLECTOR

BACKGROUND OF THE INVENTION

The present invention relates to produce recognition devices and more specifically to a hand-held produce recognition system and produce data collector.

Bar code readers are well known for their usefulness in retail checkout and inventory control. Bar code readers are capable of identifying and recording most items during a typical transaction since most items are labeled with bar codes.

Items which are typically not identified and recorded by a bar code reader are produce items, since produce items are typically not labeled with bar codes. Bar code readers may include a scale for weighing produce items to assist in determining the price of such items. But identification of produce items is still a task for the checkout operator, who must identify a produce item and then manually enter an item identification code. Operator identification methods are slow and inefficient because they typically involve a visual comparison of a produce item with pictures of produce items. Operator identification methods are also prone to error, on the order of fifteen percent.

In order to improve the accuracy of the produce recognition process, reference information on produce items must be collected and stored. Since produce items are typically located remotely from a central store server, it would be desirable to provide a hand-held produce recognition system and produce data collector.

SUMMARY OF THE INVENTION

In accordance with the teachings of the present invention, a hand-held produce recognition system and produce data collector are provided.

The produce data collector includes a light emitter for illuminating a produce item, collecting optics for collecting light reflected from the produce item and separating the reflected light into a plurality of wavelength portions of light, a photosensor for capturing wavelength information from the wavelength portions of light, control circuitry, and a hand-held housing containing the light emitter, the collecting optics, the photosensor, and the control circuitry. The control circuitry may store reference wavelength information and compare the captured wavelength information to the reference wavelength information to identify the produce item.

A method of collecting produce data includes the steps of providing a hand-held housing, illuminating a produce item through an aperture in the housing, collecting light reflected from the produce item, separating the reflected light into a plurality of wavelength portions of light, generating electrical signals for the wavelength portions of light, and converting the electrical signals to digital wavelength information. The method may include additional steps to add a recognition function, including the steps of receiving reference digital wavelength information from a computer, and comparing the digital wavelength information to the reference digital wavelength information to identify a produce item.

It is accordingly an object of the present invention to provide a hand-held produce recognition system.

It is another object of the present invention to provide a hand-held produce data collector for use by store employees who must collect reference data on produce items.

It is another object of the present invention to provide a hand-held produce data collector for use by store employees who must take inventory of produce items.

It is another object of the present invention to provide a hand-held produce data collector which communicates with a host computer.

It is another object of the present invention to provide a hand-held produce data collector which is battery powered.

It is another object of the present invention to provide a hand-held produce data collector which communicates with a host computer.

BRIEF DESCRIPTION OF THE DRAWINGS

Additional benefits and advantages of the present invention will become apparent to those skilled in the art to which this invention relates from the subsequent description of the preferred embodiments and the appended claims, taken in conjunction with the accompanying drawings, in which:

DETAILED DESCRIPTION OF THE PREFERRED EMBODIMENT

Figure 1:
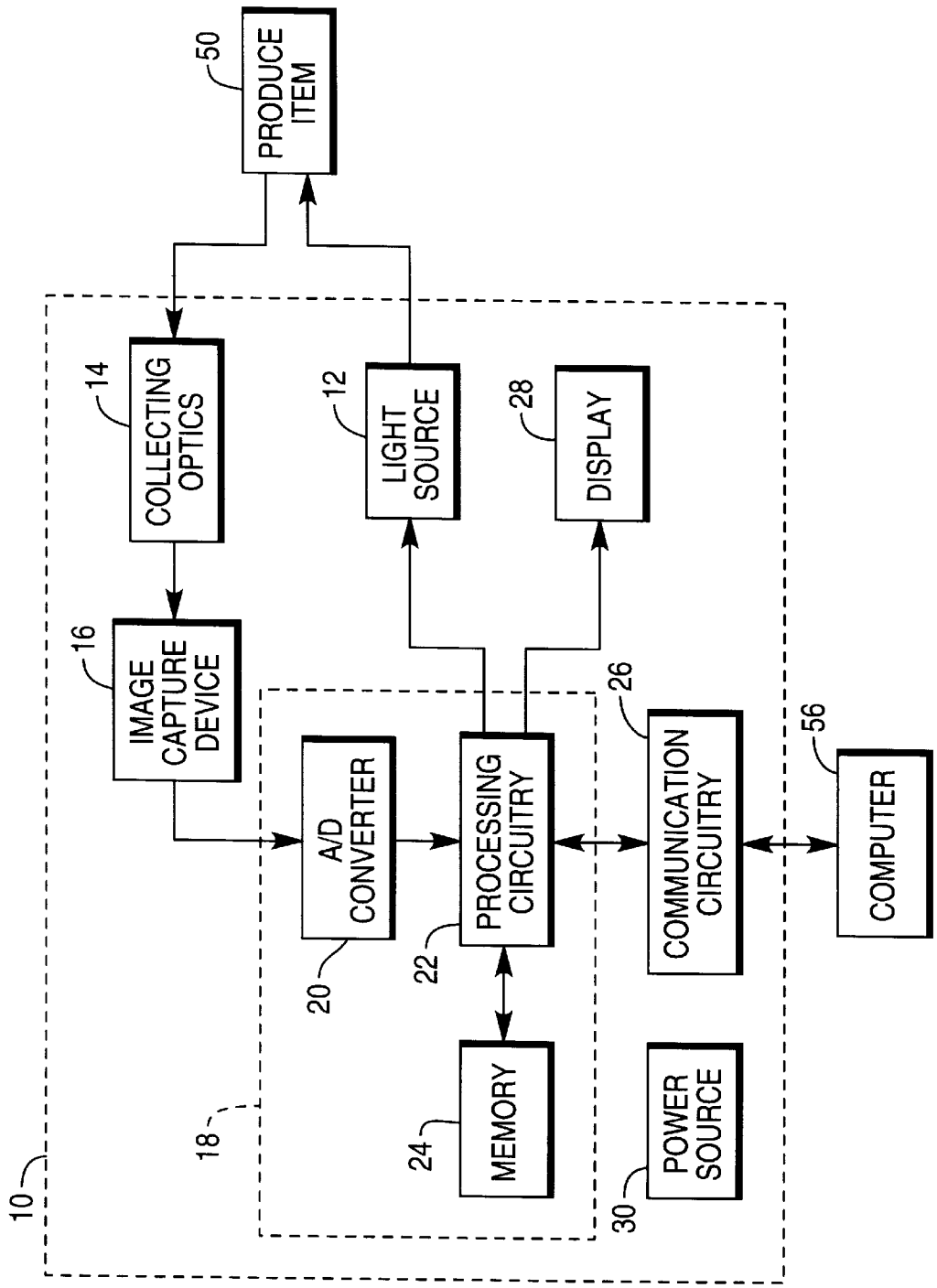
FIG. 1 is a block diagram of the hand-held produce data collector and produce recognition system.

Referring now to FIG. 1, produce recognition system 10 primarily includes light source 12, collecting optics 14, control circuitry 16, and image capture device 18.

Light source 12 produces light for illuminating produce item 50. Light source 12 preferably produces a white light spectral distribution, and preferably has a range from 400 nm to 700 nm, which corresponds to the visible wavelength region of light.

Collecting optics 14 obtains light reflected from produce item 50. Collecting optics 14 preferably includes a spectrometer or related device.

Image capture device 18 produces an electrical signal reflecting information contained in the reflected light obtained through collecting optics 14. Image capture device 18 may be any suitable photosensor or photosensor array.

Control circuitry 16 controls operation of produce recognition system 10 and produces digitized produce data. Control circuitry 16 includes analog-to-digital (A/D) converter 18, processing circuitry 20, and memory 24.

A/D converter 20 converts analog waveform signals into digital data. A twelve bit A/D converter with a sampling rate of 22–44 kHz produces acceptable results.

Processing circuitry 22 controls light source 12 and initiates produce data collection. Processing circuitry 22 identifies produce item 50 from the digital waveform data. For this purpose, processing circuitry compares the digital waveform data to reference produce data stored within memory 24. Processing circuitry 22 displays the identity of produce item 50 in display 28.

Processing circuitry 22 downloads the digital waveform data and the identification information to computer 56, such as a central server, which stores the digital produce data for future comparisons. Processing circuitry 22 also uploads reference digital produce data from computer 56 for future comparisons.

Communication circuitry 26 connects produce recognition system 10 to computer 56 to facilitate data exchange. Communication circuitry 26 may include wireless circuitry or cable-based circuitry, such as RS-232 serial communication circuitry. Communication circuitry 26 may be used to send collected digital wavelength data and identification information to computer 56, and to receive reference wavelength information from computer 56.

Power source 30 preferably includes a battery.

Figure 2:
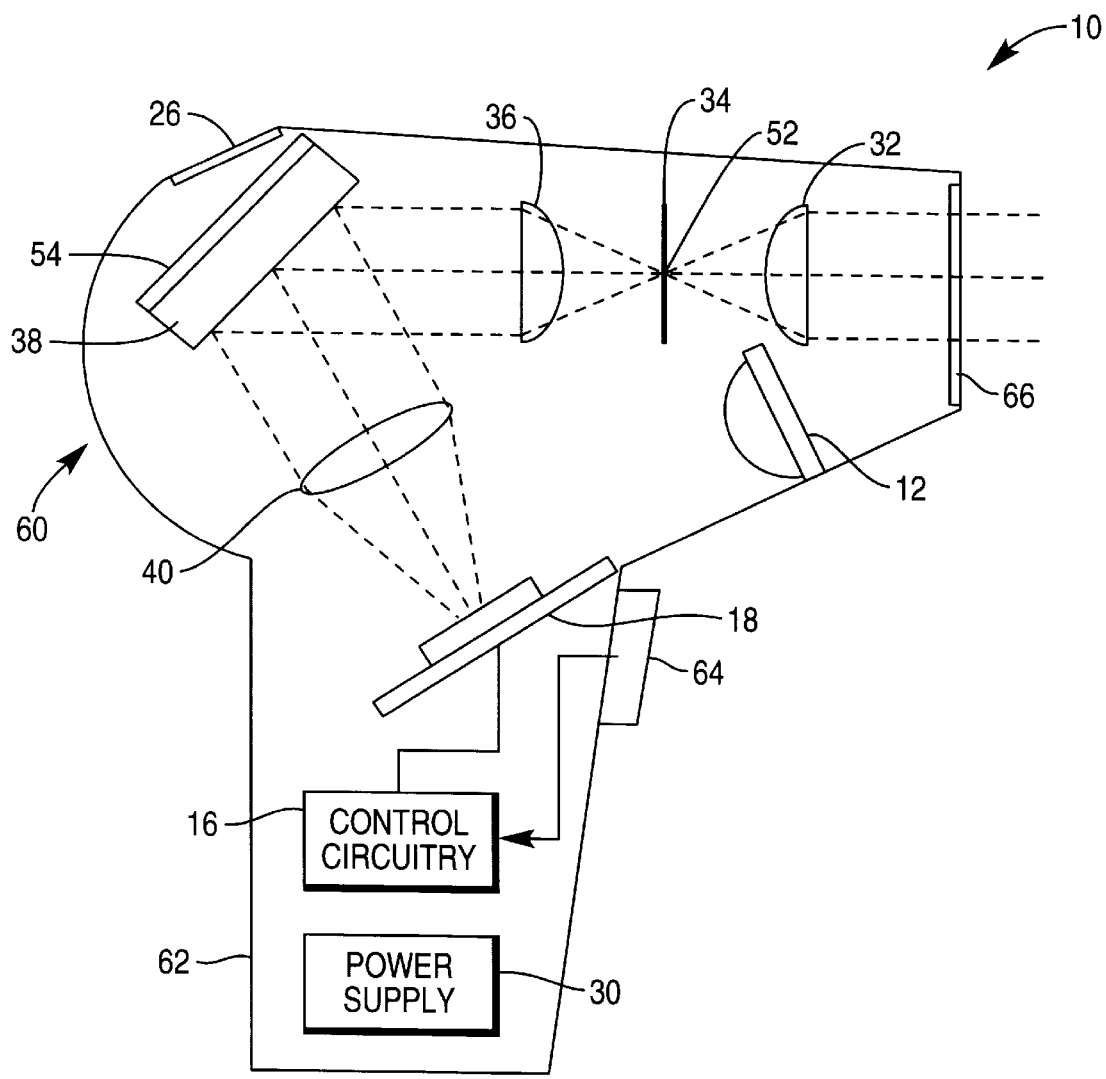
FIG. 2 is a diagrammatic view of a first embodiment of the hand-held produce data collector and produce recognition system.

Turning now to FIG. 2, a first embodiment of produce recognition system 10 is shown in more detail.

Produce recognition system includes housing 60, which includes a handle portion 62. Handle portion 62 includes trigger 64 for activating light source 12 to begin produce data collection. Housing 60 additionally includes window 66 which preferably includes an anti-reflective surface coating to prevent source light reflected from window 66 from contaminating light reflected from produce item 50.

Light source 12 preferably includes one or more light emitting diodes (LEDs). A broad-spectrum white light producing LED, such as the one manufactured by Nichia Chemical Industries, Ltd., is preferably employed because of its long life, low power consumption, fast turn-on time, low operating temperature, good directivity. Alternate embodiments include additional LEDs having different colors in narrower wavelength ranges and which are preferably used in combination with the broad-spectrum white light LED to even out variations in the spectral distribution and supplement the spectrum of the broad-spectrum white light LED.

Other types of light sources 12 are also envisioned by the present invention, although they may be less advantageous than the broad spectrum white LED. For example, a tungsten-halogen light may be used because of its broad spectrum, but produces more heat.

Collecting optics 14 places a two-dimensional image on image capture device 18 and includes collecting lens 32, linear aperture element 34, collimating lens 36, diffraction grating 38, and focusing lens 40.

Collecting lens 32 focuses reflected light from produce item 50 onto linear aperture element 34. Thus, collecting lens 32 images different spatial positions onto the surface of linear aperture element 46.

Linear aperture element 34 includes a linear aperture 52 for producing a line image. The linear aperture element may be an EDM (electro-discharge machining) cut aperture or laser cut aperture. Linear aperture element 34 restricts the input position of light into diffraction grating 38. The width of linear aperture 52 directly affects the resolution of diffraction grating 38. Linear aperture 52 is about twenty-five microns in width and about three millimeters in height.

Collimating lens 36 collimates the line image that has passed through linear aperture element 34. Collimating lens 36 is a lens element that directs light such that rays of the light are fundamentally parallel when they hit diffraction grating 38.

Diffraction grating 38 disperses the collimated line image from collimating lens 36 into a continuous band of wavelengths of light. Alternative embodiments may employ suitable alternatives, such as a prism.

Focusing lens 40 focuses the continuous band of wavelengths of light towards image capture device 18. Focusing lens 40 is a lens element that directs the now dispersed light onto image capture device 18. Focusing lens 40 collects light that is directed along the optical axis as well as off-axis light.

Space constraints require an additional optical element, mirror 54, which directs the discrete wavelengths of light towards focusing lens 40.

Image capture device 18 captures the discrete wavelengths of light and produces electrical signals containing wavelength information. Image capture device 18 is preferably a two-dimensional photosensing element, such as a two-dimensional charge coupled device (CCD) array, or a two-dimensional imaging complimentary metal oxide semiconductor (CMOS) detector. Pixel elements of image capture device 18 capture image data along discrete points of the band of wavelengths of light. The actual spatial position of a light sample on the pixels of image capture device 18 is directly related to the wavelength of the light sample.

Control circuitry 16 digitizes the electrical signals. Along a first axis of image capture device 18, the spectral variation in the received signal can be observed. Along a second axis orthogonal to the first axis, the spatial variation in the received signal can be observed.

During operation of the embodiment of FIG. 2, window 66 is placed against produce item 50. Trigger 64 is engaged to illuminate produce item 50 and initiate produce data collection and produce recognition. Control circuitry 16 identifies produce item 50 by comparing collected wavelength information with reference wavelength information in memory 24. Control circuitry 16 displays the identity of produce item 50 in display 26 and stores the identity in memory 24. Data may be exchanged with computer 56 through communication circuitry 26, both before and after use.

Figure 3:
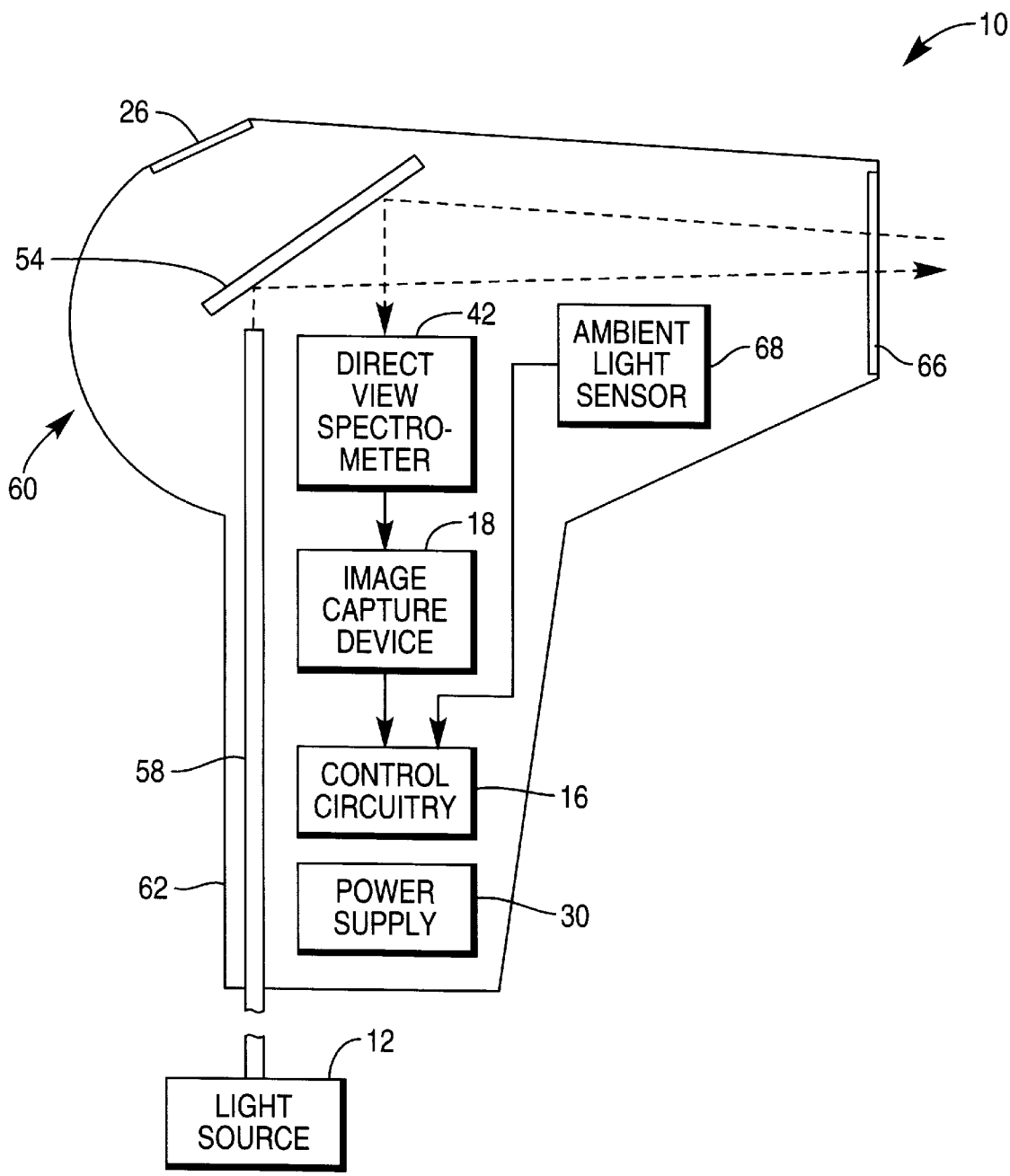
FIG. 3 is a diagrammatic view of a second embodiment of the hand-held produce data collector and produce recognition system.

Turning now to FIG. 3, a second embodiment of the produce recognition system is shown in detail.

Produce recognition system includes housing 60, as in FIG. 1.

Light source 12 is shown as externally located. Optical cable 58 carries light from light source 12. Light source 12 is preferably worn by a user on a belt, but may be mounted below handle 62. Deflecting mirror 54 directs the light towards aperture 66. Light source 12 may alternatively be located within housing 60, as in FIG. 1.

Instead of trigger 64, the second embodiment uses ambient light sensor 68 to initiate wavelength capture.

Collecting optics 14 includes direct view spectrometer 42. Direct view spectrometer 42 is a self-contained spectrometer which separates reflected light into its component wavelengths.

Image capture device 18 captures the discrete wavelengths of light and produces electrical signals containing wavelength information.

Control circuitry 16 digitizes the electrical signals.

During operation of the embodiment of FIG. 3, window 66 is placed against produce item 50. Ambient light sensor 68 automatically senses a drop in ambient light to a predetermined threshold level and initiates produce data collection and produce recognition. Control circuitry 16 identifies produce item 50 by comparing collected wavelength information with reference wavelength information in memory 24. Control circuitry 16 displays the identity of produce item 50 in display 26 and stores the identity in memory 24. Data may be exchanged with computer 56 through communication circuitry 26, both before and after use.

Advantageously, system 10 provides a portable, lightweight, produce data collector and produce recognition system for store employees. The portable nature of system 10 is beneficial to both stock and supply personnel. Also, a store employee may identify produce item 50 without picking it up.

Although the invention has been described with particular reference to certain preferred embodiments thereof, variations and modifications of the present invention can be effected within the spirit and scope of the following claims.

We claim:

1. A portable data collector comprising:
   a light emitter for illuminating a produce item;
   collecting optics for collecting light reflected from the produce item and separating the reflected light into a plurality of wavelength portions of light;
   a photosensor for capturing wavelength information from the wavelength portions of light;
   control circuitry; and
   a hand-held housing containing the light emitter, the collecting optics, the photosensor, and the control circuitry.

2. The data collector as recited in claim 1, wherein the light emitter comprises a number of light emitting diodes which together produce substantially white light.

3. The data collector as recited in claim 1, wherein the light emitter comprises:
   a light source external to the housing; and
   an optical cable which routes light from the light source into the housing.

4. The data collector as recited in claim 1, wherein the collecting optics comprises a spectrometer.

5. The data collector as recited in claim 1, wherein the control circuitry comprises:
   an analog-to-digital converter for converting analog electrical signals from the photodetector into digital wavelength information;
   a memory for storing reference wavelength information; and
   a processor for comparing the digital wavelength information to the reference wavelength information to identify the produce item.

6. The data collector as recited in claim 1, further comprising a trigger for initiating operation of the light source and collection of the wavelength information.

7. The data collector as recited in claim 1, further comprising a power supply for providing power to the control circuitry.

8. The data collector as recited in claim 7, wherein the power supply comprises a battery.

9. The data collector as recited in claim 1, further comprising communication circuitry for receiving reference wavelength information from a computer.

10. The data collector as recited in claim 9, wherein the communication circuitry comprises wireless RF communication circuitry.

11. The data collector as recited in claim 9, wherein the communication circuitry also sends the wavelength information to the computer.

12. The data collector as recited in claim 9, wherein the communication circuitry also sends produce item identification information to the computer.

13. The data collector as recited in claim 1, further comprising a display for displaying produce item identification information by the control circuitry.

14. The data collector as recited in claim 1, further comprising an ambient light sensor for initiating capture of wavelength information.

15. A portable data collector comprising:
   a light emitter for illuminating a produce item;
   a spectrometer for collecting light reflected from the produce item and separating the reflected light into a plurality of wavelength portions of light;
   a photosensor for capturing wavelength information from the wavelength portions of light and for producing corresponding analog electrical signals;
   an analog-to-digital converter for converting the analog electrical signals into digital wavelength information;
   a memory for storing the digital wavelength information;
   a processor; and
   a hand-held housing containing the spectrometer, the photosensor, the analog-to-digital converter, the memory, and the processor.

16. The portable data collector as recited in claim 15, further comprising a trigger switch for initiating collection of the digital wavelength information.

17. The portable data collector as recited in claim 15, further comprising a battery in the housing for providing power.

18. The portable data collector as recited in claim 15, further comprising a communication circuit for exchanging information with a computer.

19. The portable data collector as recited in claim 15, further comprising an ambient light sensor for initiating collection of the digital wavelength information.

20. The portable data collector as recited in claim 15, further comprising:
   a display controlled by the processor;
   wherein the processor compares the digital wavelength information to reference wavelength information to identify the produce item and display produce identification information.

21. A method of collecting produce data comprising the steps of:
   providing a hand-held housing;
   illuminating a produce item through an aperture in the housing;
   collecting light reflected from the produce item;
   separating the reflected light into a plurality of wavelength portions of light;

generating electrical signals for the wavelength portions of light; and converting the electrical signals to digital wavelength information.

22. The method as recited in claim 21, further comprising the steps of:

generating the electrical signals in response to actuation of a trigger in the housing.

23. The method as recited in claim 21, further comprising the step of:

providing power for generating the electrical signals by a battery.

24. The method as recited in claim 21, further comprising the steps of:

sensing a drop in ambient light below a predetermined threshold; and generating the electrical signals in response to the drop in ambient light.

25. The method as recited in claim 21, further comprising the step of:

sending the digital wavelength information to a computer.

26. The method as recited in claim 21, further comprising the steps of:

receiving reference digital wavelength information from a computer; and comparing the digital wavelength information to the reference digital wavelength information to identify a produce item.

27. The method as recited in claim 26, further comprising the step of:

displaying identification information.

28. The method as recited in claim 26, further comprising the step of:

sending the identification information to the computer.

\* \* \* \* \*